United States Patent
Lee et al.

(10) Patent No.: US 8,753,895 B2
(45) Date of Patent: Jun. 17, 2014

(54) SURFACE MODIFIED METAL NANO-PARTICLE AND USE THEREOF

(71) Applicant: Postech Academy-Industry Foundation, Pohang (KR)

(72) Inventors: San Joon Lee, Pohang-si (KR); Sung Yong Jung, Ulsan (KR); Sungsook Ahn, Bucheon-si (KR); Jin Pyung Lee, Pohang-si (KR); Hae Koo Kim, Yeongyang-gun (KR)

(73) Assignee: Postech Academy-Industries Foundation, Pohang (KR)

( * ) Notice: Subject to any disclaimer, the term of this patent is extended or adjusted under 35 U.S.C. 154(b) by 41 days.

(21) Appl. No.: 13/898,598

(22) Filed: May 21, 2013

(65) Prior Publication Data

US 2013/0252274 A1    Sep. 26, 2013

Related U.S. Application Data

(63) Continuation of application No. 13/169,222, filed on Jun. 27, 2011, now abandoned.

(30) Foreign Application Priority Data

Dec. 29, 2010 (KR) .................. 10-2010-0138187

(51) Int. Cl.
*G01N 24/00* (2006.01)
*G01N 23/00* (2006.01)
*G01N 21/55* (2014.01)
*G01N 21/75* (2006.01)
*B82Y 20/00* (2011.01)
*B82Y 15/00* (2011.01)
*B82Y 5/00* (2011.01)

(52) U.S. Cl.
CPC ........... *G01N 23/00* (2013.01); *B82Y 20/00* (2013.01); *B82Y 15/00* (2013.01); *G01N 21/554* (2013.01); *G01N 21/75* (2013.01); *B82Y 5/00* (2013.01); *Y10S 436/805* (2013.01); *Y10S 977/773* (2013.01); *Y10S 977/902* (2013.01); *Y10S 977/904* (2013.01)
USPC ........... 436/166; 436/805; 977/773; 977/902; 977/904; 428/402

(58) Field of Classification Search
USPC .................. 436/166, 805; 977/773, 902, 904; 428/402
See application file for complete search history.

(56) References Cited

U.S. PATENT DOCUMENTS 7,700,193 B2 * 4/2010 Chen et al. ............... 428/403
8,459,529 B2 * 6/2013 Komatsu .................. 228/56.3

* cited by examiner

*Primary Examiner* — Jill Warden
(74) *Attorney, Agent, or Firm* — Lexyoume IP Meister, PLLC.

(57) ABSTRACT

The present invention provides a metal nanoparticle that is surface-modified with a hydrophilic or hydrophobic functional group, and a composition for optical detection comprising the same. The surface-modified nanoparticles according to the present invention form clusters suitable for optical detection, for example, suitable as an X-ray contrast agent, and have surface plasmon energy in the visible region, thereby being usefully applied to a variety of optical detection methods.

20 Claims, 10 Drawing Sheets

SURFACE MODIFIED METAL NANO-PARTICLE AND USE THEREOF

CROSS-REFERENCE TO RELATED APPLICATION

This application is a Continuation Application of U.S. patent application Ser. No. 13/169,222, filed on Jun. 27, 2011, which claims priority to and the benefit of Korean Patent Application No. 10-2010-0138187 filed in the Korean Intellectual Property Office on Dec. 29, 2010, the entire contents of which are incorporated herein by reference.

BACKGROUND OF THE INVENTION (a) Field of the Invention

The present invention provides a metal nanoparticle that is surface-modified with a hydrophilic or hydrophobic functional group, and a composition for optical detection comprising the same.

(b) Description of the Related Art

Nanotechnology is a technology of manipulating and controlling matters at the atomic or molecular level, and suitable to create many new materials or devices with a vast range of applications, such as in electronics, materials, communications, mechanics, medicine, agriculture, energy and environment.

Currently, nanotechnology has been developed in various fields, and is broadly classified into three kinds of major fields: (1) nanomaterial with respect to compounding new minute matters and raw materials, (2) nanodevice with respect to manufacturing the device to function a fixed ability through arranging or mixing nano matters, and (3) nano-biotechnology with respect to applying nanotechnology to biotechnology.

In the nano-biotechnology field, nanoparticles have been used in a broad range of applications, such as separation of biomolecules, imaging contrast, and drug/gene delivery.

For more effective imaging contrast or detection, nanoparticles should form clusters within a specific range of size, have a surface plasmon in the visible region, and easily perform in vivo flow imaging. Many studies have been made on nanoparticles satisfying these requirements, but there have been no remarkable results yet.

SUMMARY OF THE INVENTION

The present inventors found that metal nanoparticles are capable of form clusters within a specific range of size when they are surface-modified with a specific functional group, thereby having a surface plasmon in the visible region, and easily performing in vivo flow imaging, to complete the present invention.

Therefore, an embodiment of the present invention provides a metal nanoparticle that is obtained by surface-modifying it with a hydrophilic or hydrophobic functional group, preferably a hydrophilic functional group.

Another embodiment provides a composition for optical detection, comprising the surface-modified nanoparticle.

DETAILED DESCRIPTION OF THE EMBODIMENTS

In the present invention, metal nanoparticles are prepared to have a suitable size and shape, and then their surface can be modified with various low molecular materials to show negatively/positively charged, acidic/basic, or hydrophilic/hydrophobic characteristics while maintaining their own properties. Such surface-modified metal nanoparticles determine important physical properties such as surface plasmon, and the metal nanoparticles are introduced into synthetic/natural microparticles to change the encapsulation efficiency.

Therefore, an embodiment of the present invention provides a metal nanoparticle that is obtained by surface-modifying with a hydrophilic or hydrophobic functional group, preferably a hydrophilic functional group. More particularly, the metal nanoparticle is characterized in that a surface-modifying material is introduced on the surface of a metal particle, the diameter of the metal particle ranges from 1 to 100 nanometer, and the surface-modifying material is one or more selected from the group consisting of aliphatic or aromatic carboxylic acids having 1 to 20 carbon atoms, pyrimidine-based bases, purine-based bases, linear or branched alcohols having 1 to 10 carbon atoms, and alkyl groups having 1 to 50 carbon atoms, preferably 1 to 20 carbon atoms.

The metal nanoparticles may be selected from the group consisting of gold, silver, magnesium oxide, iron, platinum, titanium, alumina, zirconia and the like. For example, the metal nanoparticles may be gold nanoparticles obtained by reducing a gold salt (chloride (III) trihydrate, $HAuCl_4.3H_2O$) with sodium citrate anhydride (e.g., sodium citrate tribasic dehydrate) or a suitable polymer such as a poly(ethylene-co-propylene) copolymer. The diameter of the metal nanoparticles is not particularly limited, but for the usefulness as a contrast agent, it may be 1 to 100 nm, preferably 5 to 50 nm, and more preferably 10 to 30 nm.

The surface-modifying material is directly introduced on the metal surface or introduced on the metal surface via a functional group selected from the group consisting of a thiol group, a carboxyl group, an amine group, an aldehyde group, a ketone group, a peroxide group, an alkene group having 3 to 500 carbon atoms, preferably 3 to 100 carbon atoms, more preferably 3 to 50 carbon atoms, and much more preferably 3 to 20 carbon atoms, alkyl halide having 3 to 500 carbon atoms, preferably 3 to 100 carbon atoms, more preferably 3 to 50 carbon atoms, and much more preferably 3 to 20 carbon atoms, an ester group, an ether group, an epoxide group, a nitrile group, a carbonyl group, and the like. For example, the surface-modifying material linked with a thiol group as the functional group for introduction to the metal surface may be one or more selected from the group consisting of thioglycolic acid, mercaptobenzoic acid, thioguanine, mercaptoethanol, propanethiol, terphenylthiol, propenethiol, thiazolinethiol, phenylimidazolethiol, phenylthiazolethiol, aminothiadiazolethiol, bromobenzoxazolethiol, bromopyridinethiol, fluorobenzoxazolethiol, methoxybenzoxazolethiol, carboranethiol, mentha-8-thiol-3-one, 1-(4-hydroxybenzyl)imidazole-2-thiol, 1-methyl-1H-benzimidazole-2-thiol, 1-phenyl-1H-tetrazole-5-thiol, 1H-1,2,4-Triazole-3-thiol, 3-amino-1,2,4-triazole-5-thiol, 4-(trifluoromethyl)pyrimidine-2-thiol, 4-amino-5-(4-pyridyl)-4H-1,2,4-triazole-3-thiol, 4-hydroxy-6-(trifluoromethyl)pyrimidine-2-thiol, 4-methyl-4H-1,2,4-triazole-3-thiol, 5-(3-pyridyl)-1,3,4-oxadiazole-2-thiol, 5-(4-aminophenyl)-1,3,4-oxadiazole-2-thiol, 5-(4-chlorophenyl)-1,3,4-oxadiazole-2-thiol, 5-(4-pyridyl)-1,3,4-oxadiazole-2-thiol, 5-methyl-1,3,4-thiadiazole-2-thiol, 5-methylthio-1,3,4-thiadiazole-2-thiol, 5-phenyl-1,3,4-oxadiazole-2-thiol, 5-phenyl-1H-1,2,4-triazole-3-thiol, 7-(trifluoromethyl)quinoline-4-thiol, 1-[2-(dimethylamino)ethyl]-1H-tetrazole-5-thiol, 11-(1H-pyrrol-1-yl)undecane-1-thiol, O-(2-carboxyethyl)-O'-(2-mercaptoethyl)heptaethylene glycol, O-(2-mercaptoethyl)-

O'-methyl-hexa(ethylene glycol), O-[2-(3-mercaptopropionylamino)ethyl]-O'-methylpolyethylene glycol, 1-naphthalenethiol, 11-mercapto-1-undecanol, 2-thiobarbituric acid, cysteamine hydrochloride, thiocholesterol, 1-(11-mercaptoundecyl)imidazole, spironolactone, 1-ethyltetrazole-5-thiol, 1-(3-hydroxyphenyl)-1H-tetrazole-5-thiol, 1-(2-methoxyphenyl)-4-(4-nitrophenyl)-1H-imidazole-2-thiol, 1-(3-methylphenyl)-4-(4-methylphenyl)-1H-imidazole-2-thiol hydrobromide, 1-(4-(difluoromethoxy)benzoyl)-1,4,5,6-tetrahydrocyclopenta(D)imidazole-2-thiol, 1-(4-aminophenyl)-4-phenyl-1H-imidazole-2-thiol, 1-(4-aminophenyl)tetrazole-5-thiol hydrochloride, 1-(4-aminophenyl)tetrazole-5-thiol hydrochloride, 1-methyl-1H-imidazole-2-thiol, 1-methyl-1H-tetrazole-5-thiol, 1-naphthalen-2-yl-1H-tetrazole-5-thiol, 1-phenyl-1H-(1,2,4)triazole-3-thiol, 1-(methylthio)-7H-pyrrolo(2,3-D)pyrimidine-4-thiol, 2-(methylthio)-7H-pyrrolo(2,3-D)pyrimidine-4-thiol, 1-amino-5-(2-chloro-phenyl)-pyrimidine-4-thiol, 2-amino-5-(2-chloro-phenyl)-pyrimidine-4-thiol, 2-methyl-9H-purine-6-thiol, 3-O-tolyl-6-P-tolyl-pyrazine-2-thiol, 3-phenyl-1,2,4-oxadiazole-5-thiol, 4,5-bis(4-methoxyphenyl)-4H-1,2,4-triazole-3-thiol, 4,5-dibenzyl-4H-1,2,4-triazole-3-thiol, 4,5-diphenyl-4H-1,2,4-triazole-3-thiol, 4,6-dimethyl-pyrimidine-2-thiol, 4-(2,3-dimethylphenyl)-5-methyl-4H-1,2,4-triazole-3-thiol, 4-(2,4-dimethylphenyl)-5-(4-methoxyphenyl)-4H-1,2,4-triazole-3-thiol, 4-(2,4-dimethylphenyl)-5-phenyl-4H-1,2,4-triazole-3-thiol, 4-(4-bromophenyl)-1,3-thiazole-2-thiol, 4-(4-bromophenyl)-5-(4-chlorophenyl)-4H-1,2,4-triazole-3-thiol, 4-(4-bromophenyl)-5-(4-methoxyphenyl)-4H-1,2,4-triazole-3-thiol, 4-(4-chlorophenyl)-1,3-thiazole-2-thiol, 4-(4-chlorophenyl)-5-(4-methoxyphenyl)-4H-1,2,4-triazole-3-thiol, 4-(4-ethoxyphenyl)-1,5-diphenyl-1H-imidazole-2-thiol hydrobromide, 4-(4-methoxyphenyl)-1-(4-methylphenyl)-1H-imidazole-2-thiol hydrobromide, 4-(benzylideneamino)-5-(2,4-dichlorophenyl)-4H-1,2,4-triazole-3-thiol, 4-(benzylideneamino)-5-(2-bromophenyl)-4H-1,2,4-triazole-3-thiol, 4-(benzylideneamino)-5-(2-chlorophenyl)-4H-1,2,4-triazole-3-thiol, 4-(benzylideneamino)-5-(2-fluorophenyl)-4H-1,2,4-triazole-3-thiol, 4-(benzylideneamino)-5-(2-furyl)-4H-1,2,4-triazole-3-thiol, 4-(benzylideneamino)-5-(2-methoxyphenyl)-4H-1,2,4-triazole-3-thiol, 4-(benzylideneamino)-5-(2-methylphenyl)-4H-1,2,4-triazole-3-thiol, 4-(benzylideneamino)-5-(2-pyridinyl)-4H-1,2,4-triazole-3-thiol, 4-(benzylideneamino)-5-(3,4,5-trimethoxyphenyl)-4H-1,2,4-triazole-3-thiol, 4-(benzylideneamino)-5-(3-chlorophenyl)-4H-1,2,4-triazole-3-thiol, 4-(benzylideneamino)-5-(3-ethoxyphenyl)-4H-1,2,4-triazole-3-thiol, 4-(benzylideneamino)-5-(3-isopropoxyphenyl)-4H-1,2,4-triazole-3-thiol, 4-(benzylideneamino)-5-(3-methoxyphenyl)-4H-1,2,4-triazole-3-thiol, 4-(benzylideneamino)-5-(3-methylphenyl)-4H-1,2,4-triazole-3-thiol, 4-(benzylideneamino)-5-(3-pyridinyl)-4H-1,2,4-triazole-3-thiol, 4-(benzylideneamino)-5-(4-bromophenyl)-4H-1,2,4-triazole-3-thiol, 4-(benzylideneamino)-5-(4-chlorophenyl)-4H-1,2,4-triazole-3-thiol, 4-(benzylideneamino)-5-(4-fluorophenyl)-4H-1,2,4-triazole-3-thiol, 4-(benzylideneamino)-5-(4-methoxyphenyl)-4H-1,2,4-triazole-3-thiol, 4-(benzylideneamino)-5-(4-methylphenyl)-4H-1,2,4-triazole-3-thiol, 4-(benzylideneamino)-5-(4-tert-butylphenyl)-4H-1,2,4-triazole-3-thiol, 4-(benzylideneamino)-5-(phenoxymethyl)-4H-1,2,4-triazole-3-thiol, 4-(benzylideneamino)-5-cyclohexyl-4H-1,2,4-triazole-3-thiol, 4-(benzylideneamino)-5-phenyl-4H-1,2,4-triazole-3-thiol, 4-allyl-5-phenoxymethyl-4H-(1,2,4)triazole-3-thiol, 4-amino-4H-1,2,4-triazole-3-thiol, 4-amino-5-(2,4-dichlorophenyl)-4H-1,2,4-triazole-3-thiol, 4-amino-5-(2-bromophenyl)-4H-1,2,4-triazole-3-thiol, 4-amino-5-(2-chloro-phenyl)-pyrimidine-2-thiol, 4-amino-5-(3,4,5-trimethoxyphenyl)-4H-1,2,4-triazole-3-thiol, 4-amino-5-(3-pyridinyl)-4H-1,2,4-triazole-3-thiol, 4-amino-5-(4-amino-phenyl)-pyrimidine-2-thiol, 4-amino-5-(phenoxymethyl)-4H-1,2,4-triazole-3-thiol, 4-amino-5-butyl-4H-1,2,4-triazole-3-thiol, 4-amino-5-ethyl-4H-1,2,4-triazole-3-thiol, 4-amino-5-methyl-4H-1,2,4-triazole-3-thiol, 4-benzyl-5-(2,4-dichlorophenyl)-4H-1,2,4-triazole-3-thiol, 4-benzyl-5-(3,4-dimethoxyphenyl)-4H-1,2,4-triazole-3-thiol, 4-benzyl-5-(4-pyridinyl)-4H-1,2,4-triazole-3-thiol, 4-benzyl-5-(4-tert-butylphenyl)-4H-1,2,4-triazole-3-thiol, 4-cyclohexyl-5-(2,4-dichlorophenyl)-4H-1,2,4-triazole-3-thiol, 4-cyclohexyl-5-(2-methoxyphenyl)-4H-1,2,4-triazole-3-thiol, 4-cyclohexyl-5-(3,4,5-trimethoxyphenyl)-4H-1,2,4-triazole-3-thiol, 4-cyclohexyl-5-(3,4-dimethoxyphenyl)-4H-1,2,4-triazole-3-thiol, 4-ethyl-5-(4-nitrophenyl)-4H-1,2,4-triazole-3-thiol, 4-ethyl-5-M-tolyl-4H-(1,2,4)triazole-3-thiol, 4-ethyl-5-phenoxymethyl-4H-(1,2,4)triazole-3-thiol, 4-methyl-6-trifluoromethyl-pyrimidine-2-thiol, 4-O-tolyl-5-P-tolyl-4H-(1,2,4)triazole-3-thiol, 4-phenyl-5-(3,4,5-trimethoxyphenyl)-4H-1,2,4-triazole-3-thiol, 4-phenyl-5-M-tolyl-4H-(1,2,4)triazole-3-thiol, 5,5'-(ethylenedithio)bis(1,3,4-thiadiazole-2-thiol), 5,5'-tetramethylenebis(4-phenyl-4H-1,2,4-triazole-3-thiol, 5,6,7,8-tetrahydro-quinazoline-2-thiol, 5,6-dihydro-4H-(1,3)thiazine-2-thiol, 5,7-bis(ethylamino)(1,2,4)triazolo(4,3-A)(1,3,5)triazine-3-thiol, 5-((1-naphthylmethyl)sulfanyl)-1,3,4-thiadiazole-2-thiol, 5-(2,4-dichloro-phenoxymethyl)-(1,3,4)oxadiazole-2-thiol, 5-(2,4-dichlorophenyl)-4-(4-methylphenyl)-4H-1,2,4-triazole-3-thiol, 5-(2,4-dichlorophenyl)-4-ethyl-4H-1,2,4-triazole-3-thiol, 5-(2-chloroethylthio)-1,3,4-thiadiazole-2-thiol, 5-(2-furyl)-4-(4-methoxyphenyl)-4H-1,2,4-triazole-3-thiol, 5-(3-chlorophenyl)-4-(4-fluorophenyl)-4H-1,2,4-triazole-3-thiol, 5-(3-chlorophenyl)-4-isobutyl-4H-1,2,4-triazole-3-thiol, 5-(3-methylphenyl)-4-(4-methylphenyl)-4H-1,2,4-triazole-3-thiol, 5-(4-bromophenyl)-4-(2,4-dimethylphenyl)-4H-1,2,4-triazole-3-thiol, 5-(4-bromophenyl)-4-(2-methylphenyl)-4H-1,2,4-triazole-3-thiol, 5-(4-bromophenyl)-4-(2-methylphenyl)-4H-1,2,4-triazole-3-thiol, 5-(4-chloro-phenyl)-(1,3,4)oxadiazole-2-thiol, 5-(4-chloro-phenyl)-pyrimidine-4-thiol, 5-(4-chlorophenyl)-4-(4-methoxyphenyl)-4H-1,2,4-triazole-3-thiol, 5-(4-chlorophenyl)-4-isobutyl-4H-1,2,4-triazole-3-thiol, 5-(benzylthio)-1,3,4-thiadiazole-2-thiol, 5-(butylthio)-1,3,4-thiadiazole-2-thiol, 5-(dodecylthio)-1,3,4-thiadiazole-2-thiol, 5-(ethylthio)-1,3,4-thiadiazole-2-thiol, 5-(hexylthio)-1,3,4-thiadiazole-2-thiol, 5-(pentylthio)-1,3,4-thiadiazole-2-thiol, 5-amino-1,3,4-thiadiazole-2-thiol, 5-amino-4-phenyl-4H-(1,2,4)triazole-3-thiol, 5-benzyl-4-phenyl-4H-(1,2,4)triazole-3-thiol, alkane having 3 to 500 carbon atoms, alkanethiol having 3 to 500 carbon atoms, and the like.

The metal nanoparticles surface-modified with these surface-modifying materials have a diameter of approximately 20 nm, and the interparticle distance and cluster size are suitable as an X-ray contrast agent when they form clusters in a suitable medium. Among the surface-modifying materials, gold nanoparticles surface-modified with a hydrophilic group (e.g., linear or branched alcohols having 1 to 10 carbon atoms) showed most suitable properties in flow measurements in a sap which consists mainly of water (see FIG. 2).

Further, the gold nanoparticles according to the present invention have a surface plasmon energy in the visible ray region as well as in the wavelength range from several angstroms (Å) to several micrometers (μm), and thus allow detection in the visible, X-ray and UV regions (see Example 4 and FIGS. 5a to 5e).

As described above, the surface-modified metal nanoparticles according to the present invention are useful as a composition for optical detection, and thus, another aspect of the present invention is to provide a composition for optical detection comprising the surface-modified metal nanoparticles. The composition for optical detection is characterized in that it contains the surface-modified metal nanoparticles in one or more solvents (or medium) selected from the group consisting of water, linear or branched alcohols having 3 to 500 carbon atoms, preferably 3 to 100 carbon atoms, more preferably 3 to 50 carbon atoms, and much more preferably 3 to 20 carbon atoms, aldehyde having 3 to 500 carbon atoms, preferably 3 to 100 carbon atoms, more preferably 3 to 50 carbon atoms, and much more preferably 3 to 20 carbon atoms, ketone having 3 to 500 carbon atoms, preferably 3 to 100 carbon atoms, more preferably 3 to 50 carbon atoms, and much more preferably 3 to 20 carbon atoms, and normal paraffin-based solvent having 5 to 20 carbon atoms at a concentration of 100 ppm to 10 wt %, preferably 100 to 10,000 ppm, and more preferably 100 to 1,000 ppm.

The normal paraffin-based solvent is those having a boiling point of 40° C. or lower, and for example, it may be one or more selected from the group consisting of n-pentane and isomers thereof (e.g., isopentane, neopentane, etc.), hexane, methylpentane (e.g., 2-methylpentane, 3-methylpentane, etc.), methylbutane (e.g., 2,3-dimethylbutane, 2,2-dimethylbutane, etc.), n-heptane and isomers thereof (e.g., 2-methylhexane(isoheptane), 3-methylhexane, 2,2-dimethylpentane (neoheptane), 2,3-dimethylpentane, 2,4-dimethylpentane, 3,3-dimethylpentane, 3-ethylpentane, 2,2,3-trimethylbutane, etc.), octane, n-octane and isomers thereof (e.g., 2-methylheptane, 3-methylheptane (2 enantiomers), 4-methylheptane, 3-ethylhexane, 2,2-dimethylhexane, 2,3-dimethylhexane (2 enantiomers), 2,4-dimethylhexane (2 enantiomers), 2,5-dimethylhexane, 3,3-dimethylhexane, 3,4-dimethylhexane (2 enantiomers+1 meso compound), 3-ethyl-2-methylpentane, 3-ethyl-3-methylpentane, 2,2,3-trimethylpentane (2 enantiomers), 2,2,4-trimethylpentane (isooctane), 2,3,3-trimethylpentane, 2,3,4-trimethylpentane, 2,2,3,3-tetramethylbutane, n-nonane and isomers thereof, n-decane and isomers thereof, n-undecane and isomers thereof, n-dodecane and isomers thereof, n-tridecane and isomers thereof, n-tetradecane and isomers thereof, n-pentadecane and isomers thereof, n-hexadecane and isomers thereof, n-heptadecane and isomers thereof, n-octadecane and isomers thereof, n-nonadecane and isomers thereof, n-eicosane and isomers thereof, and the like.

As aforementioned, when the surface-modified metal nanoparticles according to the present invention are included in the solvent within the above concentration range, they can form clusters suitable to act as an X-ray contrast agent, and surface plasmon energy can be easily detected in the visible ray region. Thus, it is preferable that the solvent (or medium) and concentration are adjusted within the above range. In addition, the surface-modifying material is as described above. Among them, when a hydrophilic material is used as the surface-modifying material, more excellent optical detection properties can be obtained. In the preferred embodiment, the surface-modified metal nanoparticles according to the present invention may be injected into the body at a concentration of 100 to 10 wt %, preferably 100 to 10,000 ppm, more preferably 100 to 1,000 ppm, and for example, 300 to 700 ppm in an aqueous solution.

The composition for optical detection according to the present invention means an agent that allows all types of optical analysis, such as imaging and/or spectrum analysis and/or fluorescence analysis, by measurement of in vivo optical properties of animal or plant. It can be used for X-ray contrast, UV spectroscopy (e.g., UV visible spectroscopy), fluorescence analysis, or the like.

In the present invention, the surface-modifying material forms a suitable cluster, and thus time-dependent flow motion can be easily observed in the synchrotron X-ray (see FIG. 4a). This property allows to easily measure time-dependent flow motion when the surface-modifying material is applied to plant or animal bodies (see FIG. 4b), thereby providing excellent vivo imaging contrast.

Still another aspect of the present invention is to provide a method for analyzing a biological sample using the composition for optical detection.

The method may comprise the steps of injecting the composition for optical detection into a biological sample; and detecting optical properties obtained from the biological sample.

The biological sample may be an animal or plant body, or a tissue or cell isolated from animal or plant. For example, after the composition for optical detection is injected into the biological sample, X-ray imaging or UV spectroscopy is performed, or a typical fluorescent material is added to the composition for optical detection to investigate the fluorescent properties, thereby detecting various physiological kinetic features in the animal or plant body or in the isolated tissue or cell.

In addition, a change in surface plasmon occurs by the surface modification according to the present invention, and the wavelength and intensity of light absorption/emission peaks differ depending on properties of the surface-modified material and size of the metal particles. When the surface-modified gold nanoparticles having X-ray absorption property are used as a contrast agent, the surface-modified material mainly adjusts physical properties that influence interparticle relations. In molecular detection using the surface plasmon properties, the property of changing energy detection region is important as a contrast agent. The wavelength and intensity of light absorption/emission peaks are changed, and a specific reaction can be monitored by observing the changes in both the wavelength and intensity due to interactions between nanoparticles and a target to be detected.

The metal nanoparticles of the present invention are surface-modified with a specific surface-modifying material, and thus they have a uniform size, and the interparticle distance and cluster size become suitable as an X-ray contrast agent when they form clusters in a suitable medium, and they have favorable surface plasmon properties in a wide range of regions including the visible region, thereby being usefully applied as a composition for optical detection.

EXAMPLES

Hereinafter, the present invention will be described in more detail with reference to the following Examples. However, these Examples are for illustrative purposes only, and the invention is not intended to be limited by these Examples.

Example 1

Preparation of Surface-Modified Gold Nanoparticles

Gold chloride (III) trihydrate ($HAuCl_4 \cdot 3H_2O$) was dissolved in de-ionized water to prepare a solution of $1.0 \times 10^{-3}$ mol/L, and 20 mL of sodium citrate tribasic dehydrate solution in water ($4 \times 10^{-2}$ mol/L) was added to 200 mL of the above solution under refluxing, thereby reducing the surface of gold particles. After refluxing for 30 min, the temperature was reduced to 25° C., and the particle size was adjusted to approximately 20 nm. After completion of the reduction, the final particles were dialyzed in de-ionized water overnight using Spectra/Por® 7 membrane (1,000 Da cut) to remove unreacted impurities.

Figure 1:
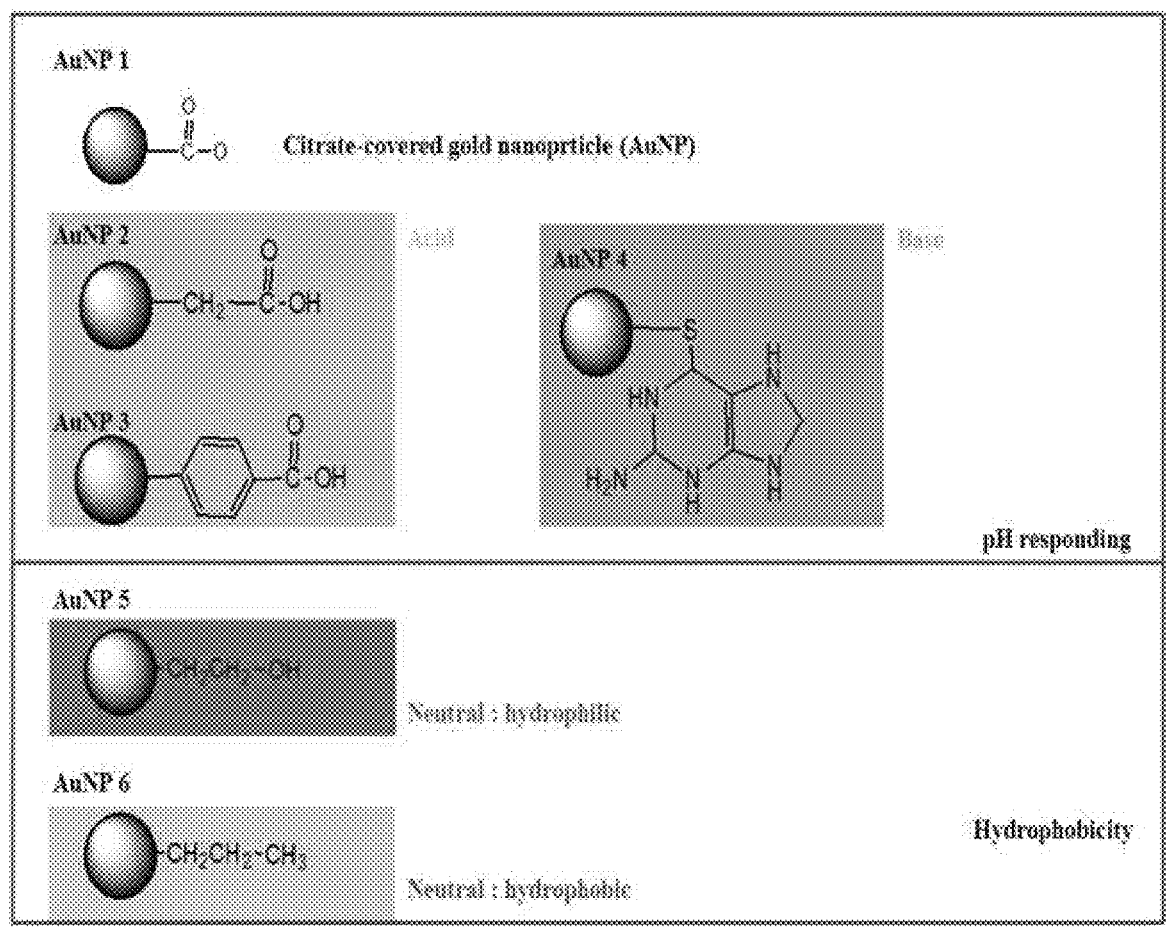
FIG. 1 is a diagram showing gold nanoparticles prepared in Example 1.

The particles prepared without additional reaction after the reduction were designated as AuNP 1. 40 mL of 0.1 M thioglycolic acid ($SH-CH_2COOH$), 40 mL of 0.1 M 4-mercaptobenzoic acid ($SH-Ph-COOH$), 40 mL of 0.1 M 6-thioguanine ($SH-C_5H_4N_5$), 40 mL of 0.1 M 2-mercaptoethanol ($SH-CH_2CH_2OH$), and 40 mL of 0.1 M 1-propanethiol ($SH-CH_2CH_2CH_3$) were added to 10 ml of the reduced particle in de-ionized water ($2.4 \times 10^{18}$ AuNPs/m$^3$) at room temperature, and then reacted at 50 to 60° C. for 6 to 12 hrs until there is no more change in color. After completion of the reaction, the particles were dialyzed in de-ionized water overnight using Spectra/Por® 7 membrane (1,000 Da cut) to remove unreacted impurities. The obtained particles were designated as AuNP 2 (modified with $SH-CH_2COOH$), AuNP 3 (modified with SH-Ph-COOH), AuNP 4 (modified with $SH-C_5H_4N_5$), AuNP 5 (modified with $SH-CH_2CH_2OH$), and AuNP 6 (modified with $SH-CH_2CH_2CH_3$), respectively (see FIG. 1).

Figure 2A:
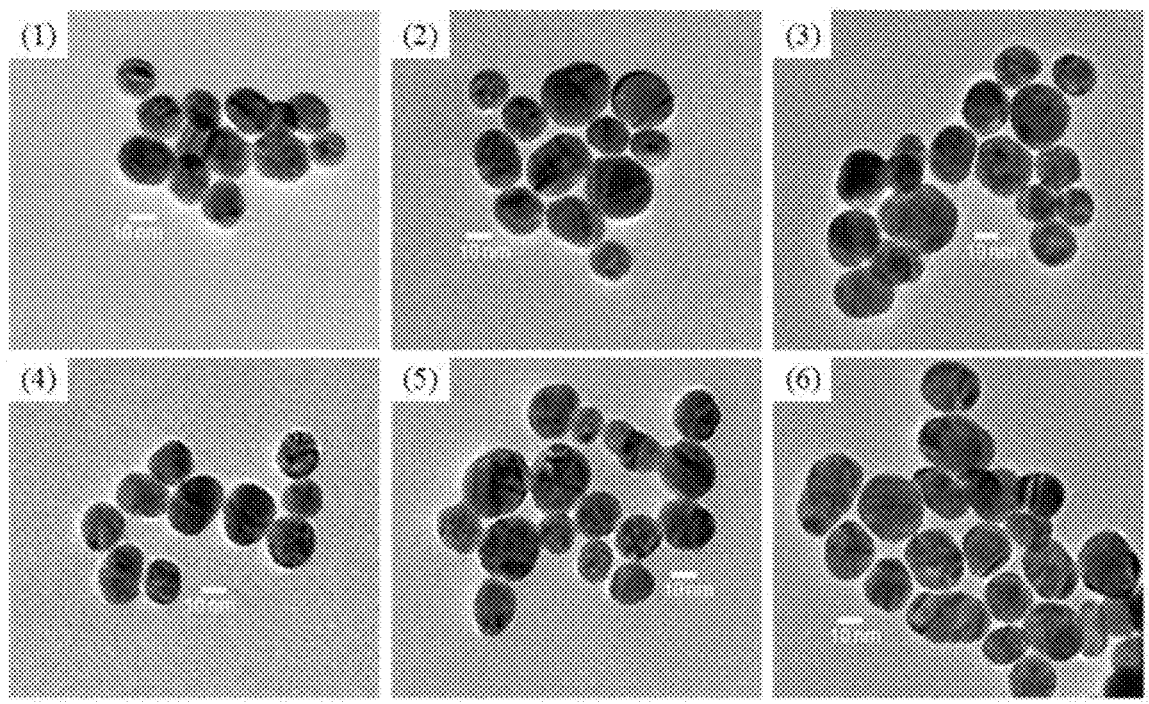
FIG. 2a shows six types of gold nanoparticles prepared in Example 1.

Transmission electron microscopy (TEM) images (JEOL Cs-corrected HR-TEM (JEM-2200FS)) of the obtained six gold nanoparticles, AuNP 1, AuNP 2, AuNP 3, AuNP 4, AuNP 5, and AuNP 6 are shown in FIG. 2a. As shown in FIG. 2a, it was confirmed that the average diameter of all gold nanoparticles was constantly controlled in a nanosize.

Figure 2B:
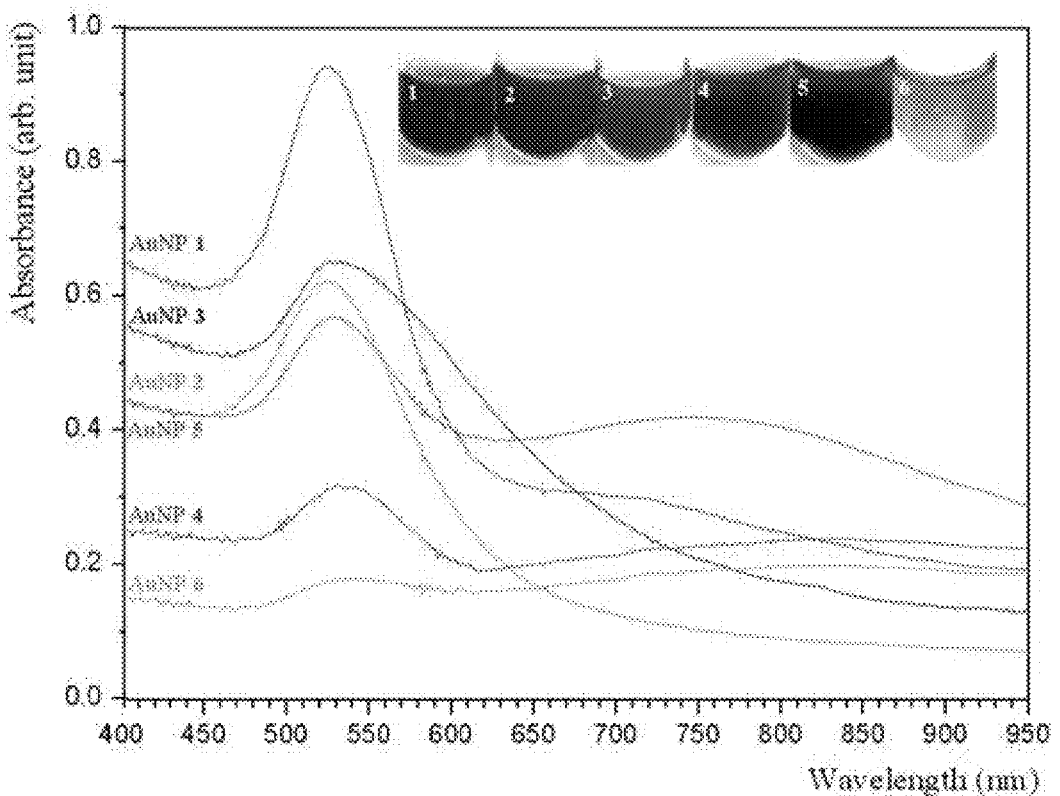
FIG. 2b shows surface plasmon properties according to surface-modification, in which each numeral means the number of AuNP of FIG. 1.

In addition, the obtained six gold nanoparticles, AuNP 1, AuNP 2, AuNP 3, AuNP 4, AuNP 5, and AuNP 6 were dissolved in de-ionized water to prepare solutions of $2.4 \times 10^{18}$ AuNPs/m$^3$, respectively, and their absorbance according to wavelength was measured using a UV-vis spectrometer (HP, HP8453), and the results are shown in FIG. 2b.

As shown in FIG. 2b, the AuNPs 1 and 2 had a main peak at 524 nm, but the intensity of the peak was lower in AuNP 2, indicating that cluster formation easily occurs in AuNP 2 compared to AuNP 1. AuNP 3 had a main peak at 527 nm, and the main peak was red-shifted to 529 nm in alcohol-functionalized AuNP 5. Meanwhile, the main peaks of 6-thioguanine-functionalized AuNP 4 and methyl-functionalized AuNP 6 were red-shifted to 537 nm with lower intensity. The absorbance of AuNPs 5 and 6 gradually increases with the increase in the wavelength. AuNP 5 exhibits another prominent peak at 770 nm. Overall, it was found that the main peaks at around ~520 nm were peak-broadened and red-shifted due to the surface modification with hydrophilic/hydrophobic, or acidic/basic functional group.

As shown in FIG. 2a, the gold nanoparticles were controlled to have the size of approximately 20 nm. However, solution properties shown in FIG. 2b were changed by surface plasmon according to surface modification of the gold nanoparticles.

FIG. 2b shows the absorption spectra of the AuNPs from 1 to 6 designed in the present Example that were dispersed in de-ionized water, together with the picture images of the solutions. AuNPs 1 and 2 exhibited deep red wine color, while AuNPs 3 and 5 expressed bluish red wine color. AuNPs 4 and 6, on the other hand, had an apparently bluish color. The absorption was measured by a UV-vis spectrometer (HP, HP8453). AuNPs 1 and 2 had a main peak at about 524 nm, but the intensity of the peak is lower in AuNP 2. That main peak was found to be red-shifted to 527 nm in AuNP 3. Hydrophilic alcohol-covered AuNP 5 shows the main peak approximately at 529 nm with lower intensity. Meanwhile, the main peaks of 6-thioguanine-covered AuNP 4 and methyl-covered AuNP 6 were positioned at around 537 nm with far lower intensity. The absorption of AuNPs 5 and 6 gradually increased with the increase in the wavelength. AuNP 5 exhibited second peak at around 770 nm. Overall, the absorbance intensity of the main peaks (~520 nm) was decreased with a peak broadening and red-shifted to higher wavelength region, as the surface ligand becomes neutral and hydrophobic.

Example 2

Cluster Formation of Surface-Modified Gold Nanoparticles

AuNP 1, AuNP 2, AuNP 3, AuNP 4, AuNP 5, and AuNP 6 were dissolved in de-ionized water at a concentration of 2.4×

Figure 3A:
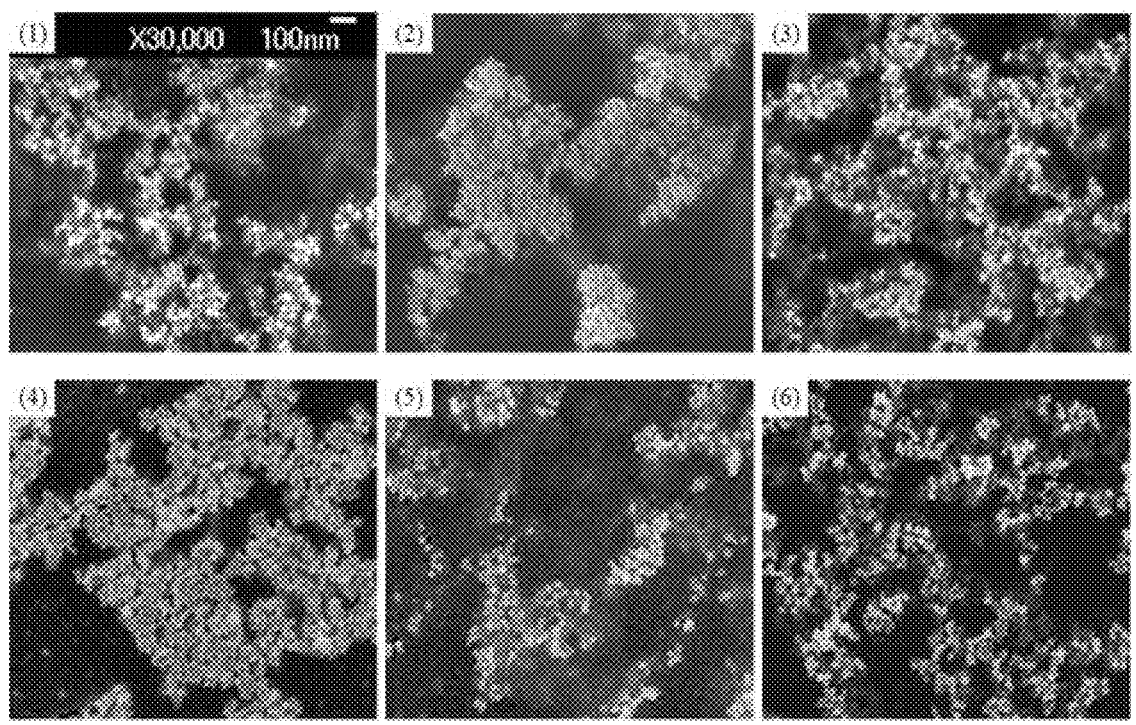
FIGS. 3a and 3b show particle formation characteristics in a nanoscale (average number of particles in 200×200 $nm^2$ and interparticle distance, a) and cluster formation characteristics in a microscale (average number and size of clusters, b) according to properties of the surface-modifying materials of six types of gold nanoparticles prepared in Example 1.
Figure 3A:
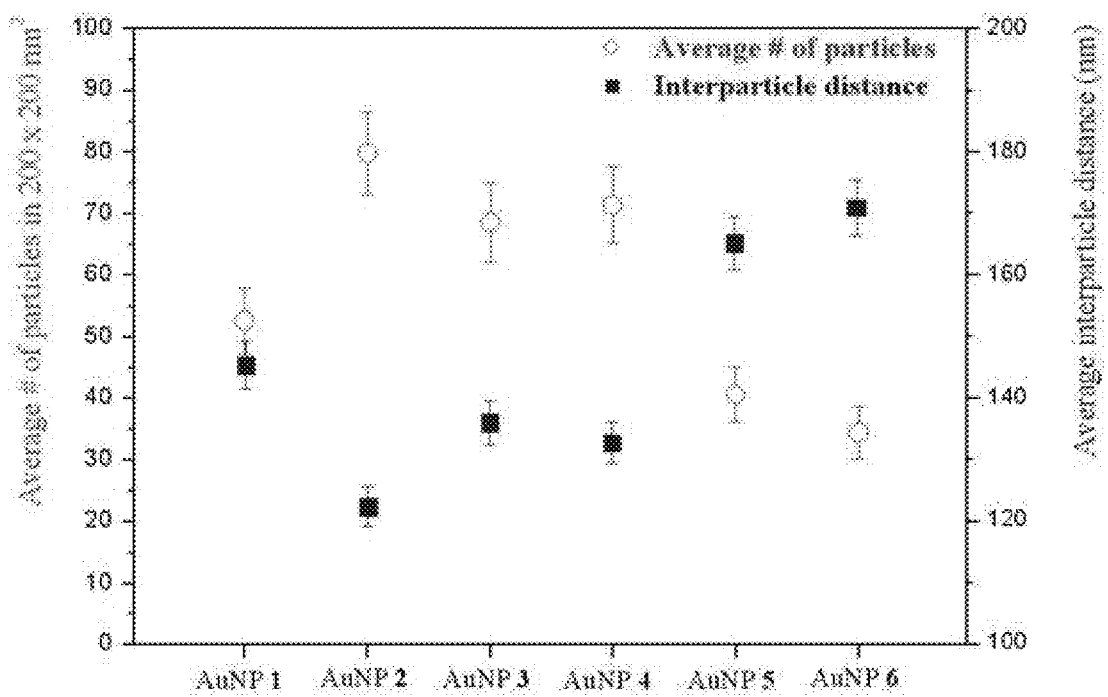
Figure 3B:
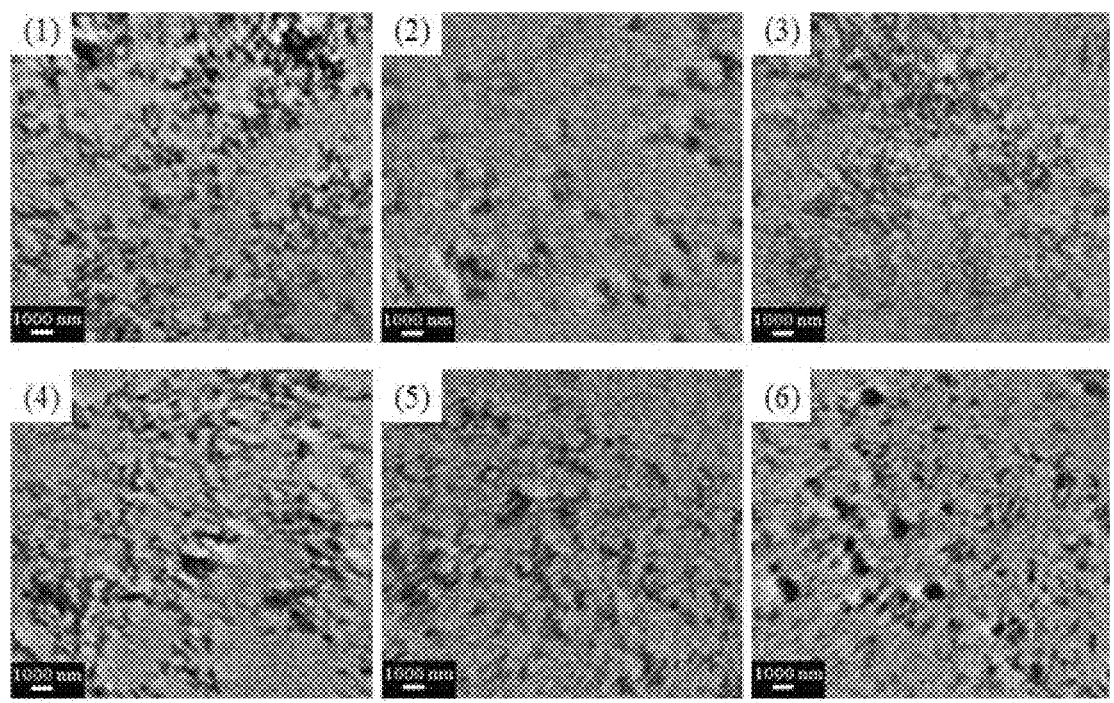
Figure 3B:
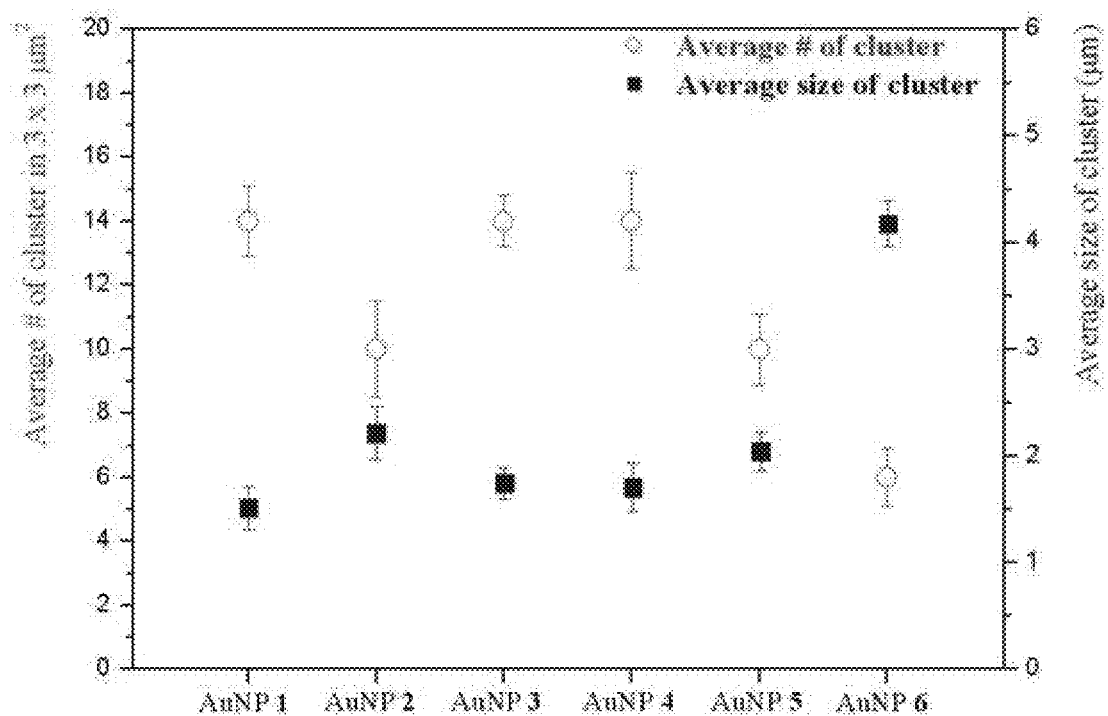

$10^{18}$ AuNPs/m$^3$, respectively. Each of the solutions was dropped on a slide glass, and dried. Their images were obtained by scanning electron microscopy (SEM) (JEOL JSM-7401F SEM at an acceleration voltage of 15 kV) (3a) and zone-plate X-ray nanoscopy (3b), and shown in the upper part of FIGS. 3a and 3b. The number described in each picture corresponds to the particle number of FIG. 1. The average interparticle distance and average size of the clusters in 20 predetermined areas (200×200 nm$^2$ and 3×3 mm$^2$) are shown in the graph of the lower part of each figure.

Example 3

Imaging of Sap Flow Using Surface-Modified Particles

It was tested whether the physical properties of the gold nanoparticles fabricated according to the present invention are controlled, and thus time-dependent flow motion of the clusters can be measured in the synchrotron X-ray. The gold nanoparticle used in the test was AuNP 5 suggested in FIG. 1. Starting from the concentration of $2.4 \times 10^{18}$ AuNPs/m$^3$, the concentration was increased 10 times to reach $2.4 \times 10^{19}$ AuNPs/m$^3$. Upon converting it into a weight of 20 nm gold nanoparticle, its concentration is 500 mg/kg H$_2$O (500 ppm).

Figure 4A:
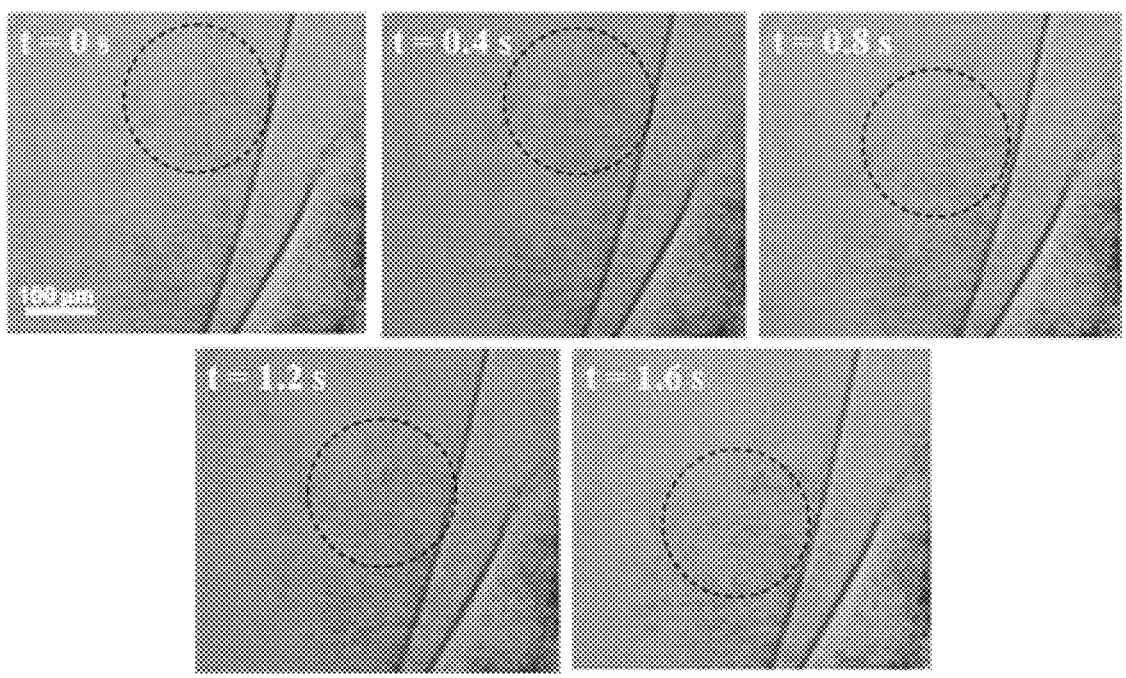
FIG. 4a is X-ray images showing time-dependent flow motions of AuNP5 (gold nanoparticle surface-modified with a hydrophilic group, namely, an ethanol group) among the gold nanoparticles prepared in Example 1.

The flow motion of the clusters was measured using the synchrotron X-ray. The synchrotron X-ray source was obtained from 7B2 beamline at the Pohang Accelerator Laboratory (Pohang, Korea). Using a bending magnet, X-rays with a peak energy of 20.3 keV (8-30 keV range) were applied as a function of time without monochromator to obtain high energy. A CdWO$_4$ crystal was used as a scintillator to convert the X-ray into visible wavelength. A charge coupled device (CCD) camera was used to convert the optical brightness into electrical signals. Time-resolved images were captured through the Kapton film covering a sample holder at a speed rate of 25 frames per second. Starting from the concentration of $2.4 \times 10^{18}$ AuNPs/m$^3$, the concentration of the gold nanoparticles was gradually increased to measure the time-dependent flow motion. When the concentration of the gold nanoparticle reached $2.4 \times 10^{19}$ AuNPs/m$^3$ (10 times), the flow motion can be visualized as shown in FIG. 4a, indicating optical intensity suitable to capture images.

Figure 4B:
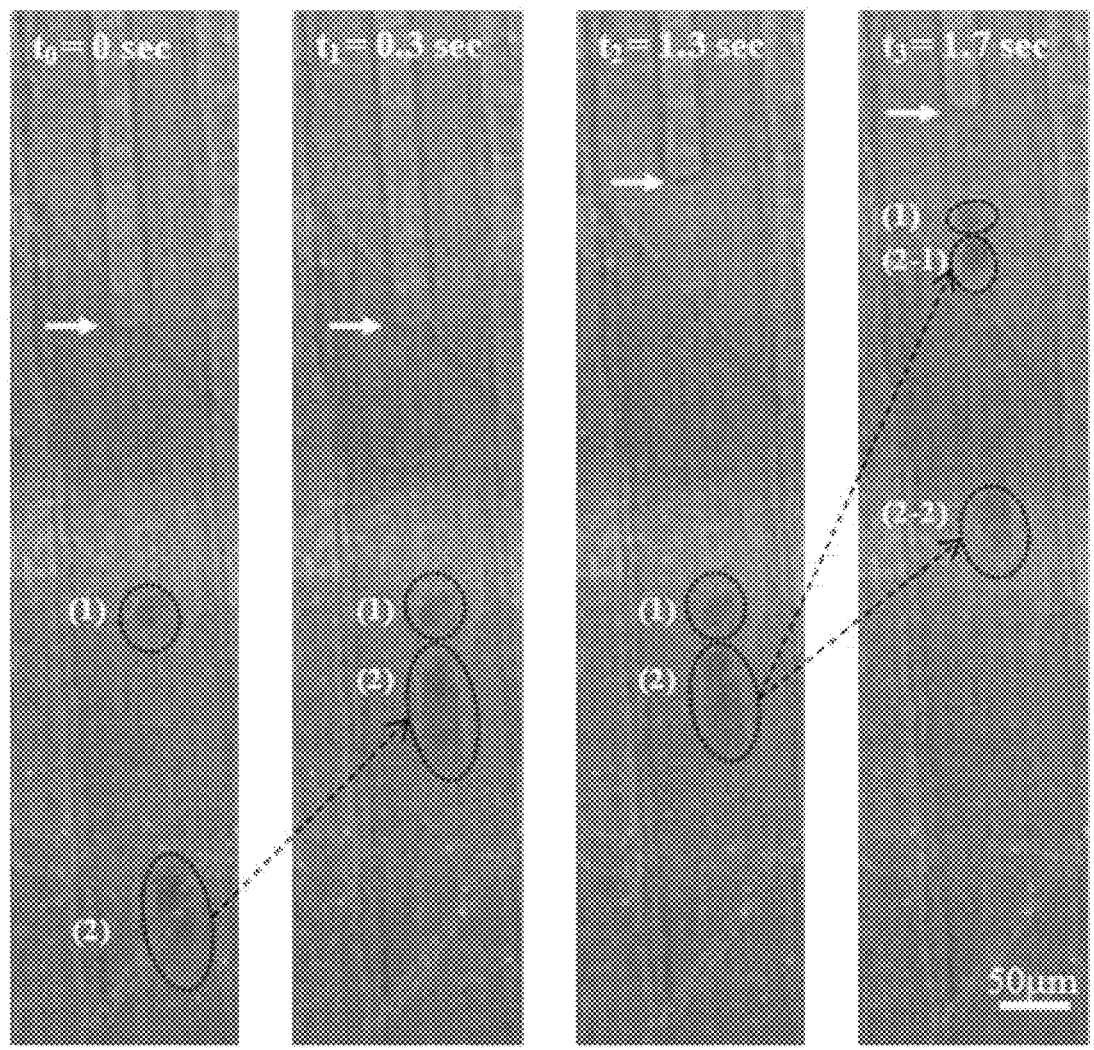
FIG. 4b is X-ray images showing time-dependent flow motions across xylem vessels in a rice monitored by AuNP5 (gold nanoparticle surface-modified with a hydrophilic group, namely, an ethanol group)

The gold nanoparticles were used to track sap flow motions in plants, and consecutive images showing the time-dependent flow motions of the gold nanoparticles inside the xylem vessels of a rice leaf are shown in FIG. 4b. After the concentration-controlled gold nanoparticle (AuNP 5) solution was taken up by the rice leaf, time-dependent images were captured using the above described X-ray imaging technique.

More particularly, the leaf end of rice (Oryza sativa (L.) cv Dongjin) was cut, and left for about 5 min until the xylem vessels were dehydrated. Then, the leaf end was dipped for about 10 min in the solution of $2.4 \times 10^{19}$ AuNPs/m$^3$, which was prepared by dissolving AuNP 5 in de-ionized water, and transport of the gold nanoparticle solution inside the xylem vessels through the root was observed.

The uptake of the gold nanoparticle solution inside the xylem vessels of a rice leaf was visualized by X-ray imaging (X-ray radiography) to observe the time-dependent flow motions of the nanoparticles, as shown in FIG. 4b. The arrows in the images of FIG. 4b indicate the meniscus, and flow motions have been understood by tracing the meniscus in the conventional studies. As shown in FIG. 4b, it was found that the sap flow motions inside the xylem vessels (1) and (2) differ from the meniscus. (1) and (2) represent the initial positions of the AuNP clusters and it was observed that (1) did not move and remained stationary and only (2) moved until 1.3 sec. (1) remained stationary due to the flow resistances produced by a perforation plate. At the time of 1.7 sec, when pulling capacity to overcome the flow resistance was applied, it moved again. Because of insufficient pulling capacity, the clusters at (2) divided into (2-1) and (2-2).

This result demonstrates that the gold nanoparticles of the present invention actually operate as an effective contrast agent suitable for in vivo exploration.

Example 4

Surface Plasmon Energy of Surface-Modified Gold Nanoparticle in Visible Region

A gold (III) chloride trihydrate (HAuCl$_4$.3H$_2$O, 0.5 g/200 mL water) solution was mixed with Pluronic 84 to prepare gold nanoparticles by reduction.

More particularly, the gold (III) chloride trihydrate aqueous solution (0.5 g/200 mL water) and Pluronic 84 were mixed with each other in a weight ratio of 0.9:0.1, 0.8:0.2, 0.7:0.3, 0.6:0.4, 0.5:0.5, 0.4:0.6, 0.3:0.7, 0.2:0.8, and 0.1:0.9 (weight of gold (III) chloride trihydrate aqueous solution: weight of Pluronic 84) to prepare gold nanoparticles by reduction of gold (III) chloride trihydrate.

Figure 5A:
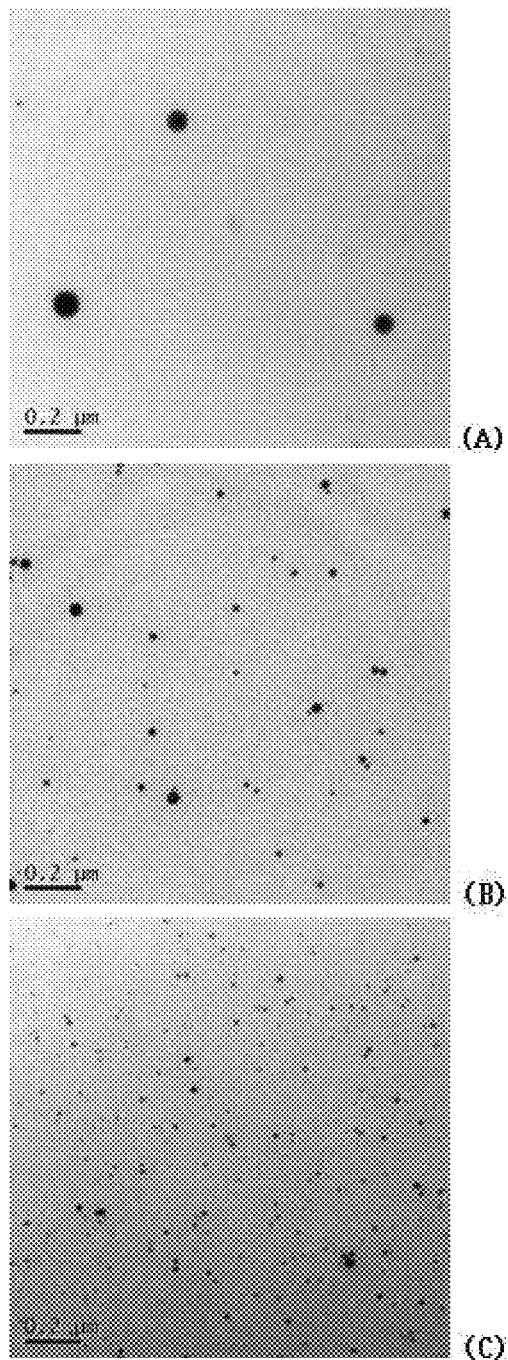
FIG. 5a shows the size of gold nanoparticles prepared by reduction of gold metal ions with a triblock copolymer (Pluronic) composed of poly(ethylene-co-propylene), in which (A) shows gold nanoparticles reduced with 10 wt % of Pluronic P84, (B) shows gold nanoparticles reduced with 30 wt % of Pluronic P84, and (C) shows gold nanoparticles reduced with 50 wt % of Pluronic P84.

Among them, the gold nanoparticles obtained by mixing the gold (III) chloride trihydrate aqueous solution and Pluronic 84 in a weight ratio of 0.9:0.1 [FIG. 5a (A)], 0.7:0.3 [FIG. 5a (B)], and 0.5:0.5 [FIG. 5a (C)] are shown in FIG. 5a.

Figure 5B:
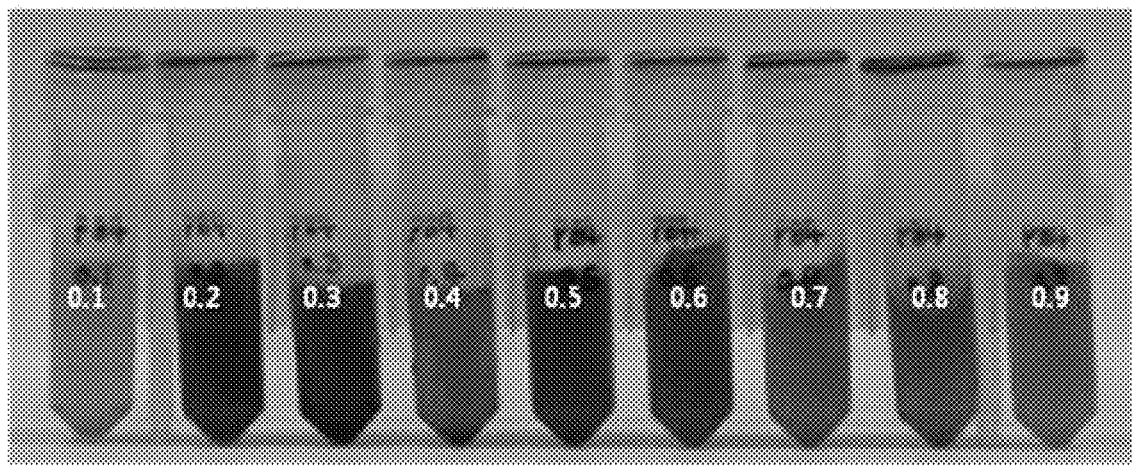
FIG. 5b shows color changes by addition of gold nanoparticle to the amphiphilic polymer Pluronic 84 dissolved in water, indicating surface plasmon energy in the visible region.

In addition, when nanoparticles were prepared by reducing the gold (III) chloride trihydrate with various concentrations of Pluronic 84, changes in color were shown as in FIG. 5b. The numbers in FIG. 5b represent the weight ratio of Pluronic 84, when a total weight of the mixture of the gold (III) chloride trihydrate aqueous solution and Pluronic 84 is regarded as 1. As shown in FIG. 5b, upon addition of the gold nanoparticles to the amphiphilic polymer Pluronic 84 dissolved in water, unique color changes are shown depending on the polymer concentration, indicating that they have surface plasmon energy in the visible region.

Figure 5C:
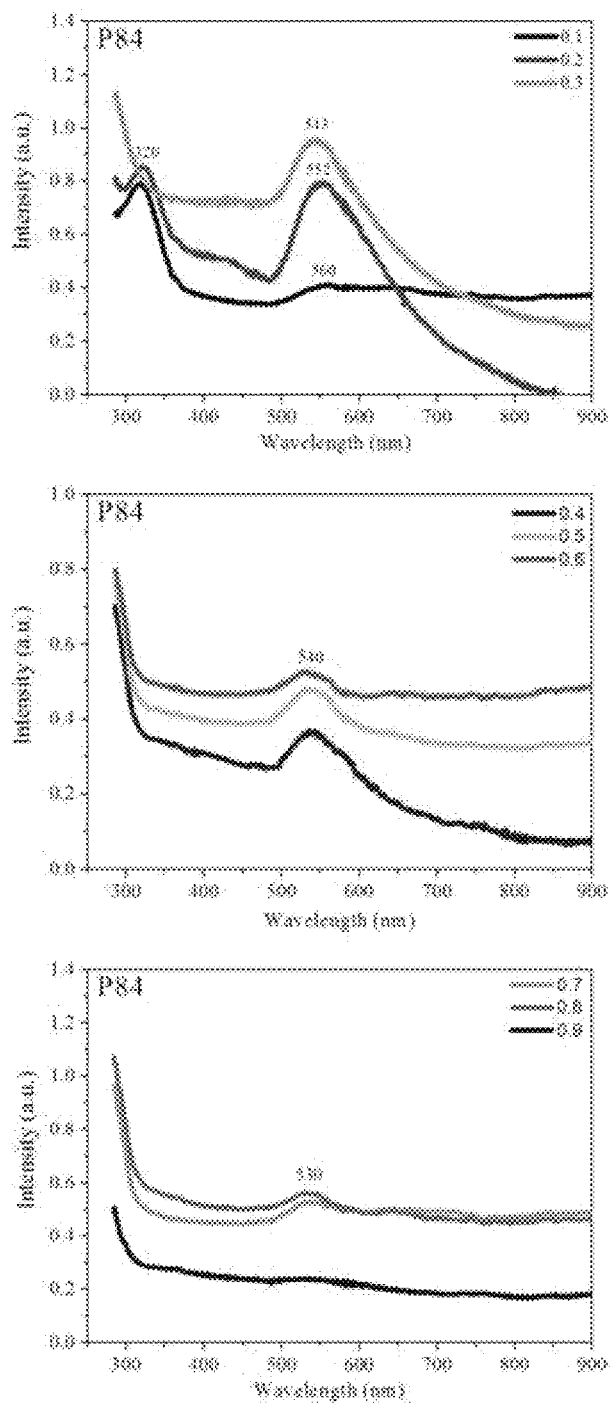
FIG. 5c shows the results of UV-vis spectroscopy measuring surface plasmon energy of the particles in FIG. 5b.

In addition, the surface plasmon energy was measured at each concentration using a UV-vis spectrometer (HP, HP8453), and the results are shown in FIG. 5c. As shown in FIG. 5c, a weak peak was observed at the weight ratio of Pluronic 84 of 0.1 and 0.9, indicating that particle formation occurs unclearly or no particle formation occurs in the measured energy region. Formation of gold nanoparticles having surface plasmon energy in the measured region was observed at the weight ratio of Pluronic 84 from 0.2 to 0.8.

Figure 5D:
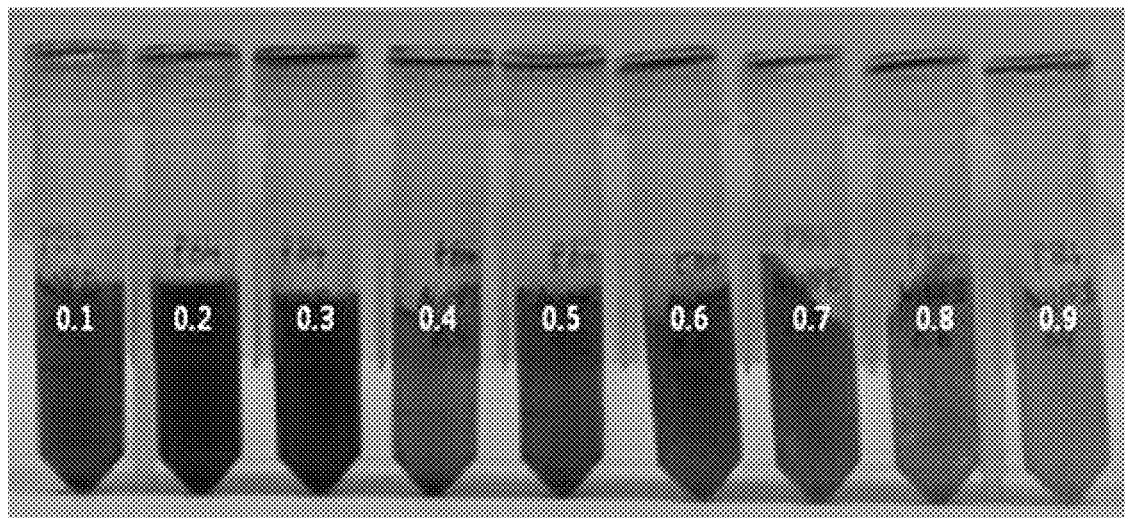
FIG. 5d shows color changes by addition of AuNP 5 (among the hydrophilic gold nanoparticles in FIG. 1) to the amphiphilic polymer Pluronic 84 dissolved in water, indicating surface plasmon energy in the visible region.

Among the gold nanoparticles prepared in Example 1, the hydrophilic (SH—CH$_2$CH$_2$OH)-covered AuNP 5 was added to various concentrations of the Pluronic 84 aqueous solution, and the concentration-dependent color change was observed and shown in FIG. 5d. The numbers in FIG. 5d represent the concentrations of the Pluronic 84 aqueous solution, and are the same as in FIG. 5b. As shown in FIG. 5d, it can be seen that the hydrophilic gold nanoparticles according to the present invention exhibit unique surface plasmon in the visible region within the microstructures of various concentrations of Pluronic 84.

Figure 5E:
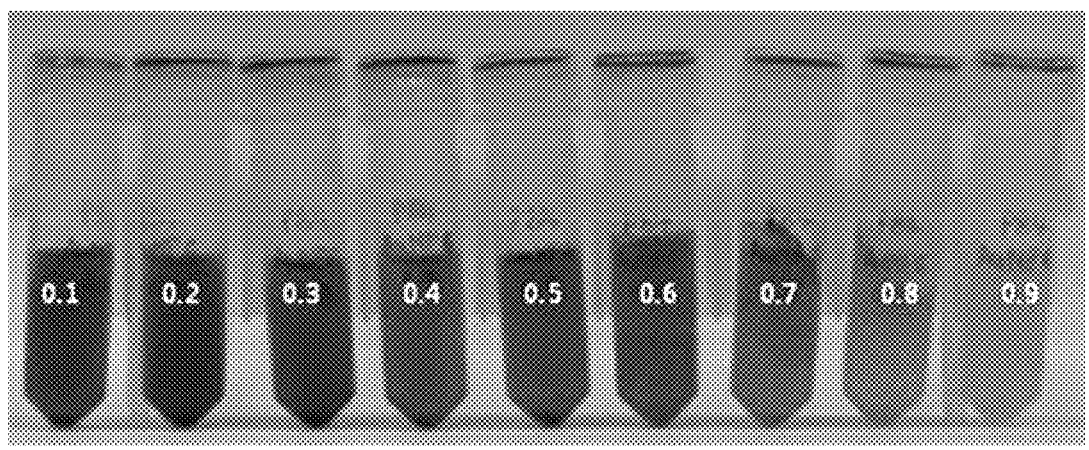
FIG. 5e shows color changes by addition of AuNP 6 (among the hydrophobic gold nanoparticles in FIG. 1) to the amphiphilic polymer Pluronic 84 dissolved in water, indicating surface plasmon energy in the visible region (0.1 to 0.9 marked on the test tubes of FIGS. 5b, 5d and 5e represent the concentrations of Pluronic 84, and 0.1 means 10% by weight, 0.2 20% by weight, 0.3 30% by weight, 0.4 40% by weight, 0.5 50% by weight, 0.6 60% by weight, 0.7 70% by weight, 0.8 80% by weight, and 0.9 90% by weight.

Among the gold nanoparticles prepared in Example 1, the hydrophobic (SH—CH$_2$CH$_2$CH$_3$)-covered AuNP 6 was added to various concentrations of the Pluronic 84 aqueous solution, and the concentration-dependent color change was observed and shown in FIG. 5e. The numbers in FIG. 5e represent the concentrations of the Pluronic 84 aqueous solution, and are the same as in FIG. 5b. As shown in FIG. 5e, it can be seen that the hydrophobic surface modified gold nanoparticles according to the present invention exhibit unique surface plasmon in the visible region within the microstructures of various concentrations of Pluronic 84.

What is claimed is:

1. A method for optically detecting a biological sample using a surface-modified metal nanoparticle, the method comprising:
   introducing a surface-modifying material to a metal nanoparticle;
   injecting a composition comprising the surface-modified metal nanoparticle into the biological sample; and
   detecting the biological sample by performing X-ray imaging, UV spectroscopy, or fluorescence analysis of the surface-modifying material of the surface-modified metal nanoparticle,
   wherein a particle diameter of the metal nanoparticle ranges from 10 to 30 nm, and
   wherein the surface-modifying material is mercaptoethanol.

2. The method according to claim 1, wherein the metal nanoparticle is selected from the group consisting of gold, silver, magnesium oxide, iron, platinum, titanium, alumina, and zirconia.

3. The method according to claim 1, wherein the surface-modifying material is introduced on the metal nanoparticle surface through a functional group selected from the group consisting of thiol group, carboxyl group, amine group, aldehyde group, ketone group, peroxide group, alkene group having 3 to 500 carbon atoms, alkyl halide having 3 to 500 carbon atoms, ester group, ether group, epoxide group, nitrile group, and carbonyl group.

4. The method according to claim 1, wherein the biological sample is an animal or plant body, or a tissue or cell isolated from animal or plant.

5. The method according to claim 1, wherein the composition is included in one or more solvents at a concentration of 100 ppm to 10 wt %, wherein the one or more solvents are selected from the group consisting of water, linear or branched alcohol having 3 to 500 carbon atoms, aldehyde having 3 to 500 carbon atoms, ketone having 3 to 500 carbon atoms, and normal paraffin-based solvent having 5 to 20 carbon atoms.

6. The method according to claim 2, wherein the metal nanoparticle is gold.

7. The method according to claim 2, wherein the metal nanoparticle is magnesium oxide.

8. The method according to claim 2, wherein the metal nanoparticle is iron.

9. The method according to claim 2, wherein the metal nanoparticle is platinum.

10. The method according to claim 2, wherein the metal nanoparticle is titanium.

11. The method according to claim 2, wherein the metal nanoparticle is alumina.

12. The method according to claim 2, wherein the metal nanoparticle is zirconia.

13. The method according to claim 3, wherein the surface-modifying material is introduced on the metal nanoparticle surface through the thiol group.

14. The method according to claim 3, wherein the surface-modifying material is introduced on the metal nanoparticle surface through the carboxyl group.

15. The method according to claim 3, wherein the surface-modifying material is introduced on the metal nanoparticle surface through the amine group.

16. The method according to claim 3, wherein the surface-modifying material is introduced on the metal nanoparticle surface through the ketone group.

17. The method according to claim 3, wherein the surface-modifying material is introduced on the metal nanoparticle surface through the peroxide group.

18. The method according to claim 3, wherein the surface-modifying material is introduced on the metal nanoparticle surface through the ester group.

19. The method according to claim 3, wherein the surface-modifying material is introduced on the metal nanoparticle surface through the ether group.

20. The method according to claim 3, wherein the surface-modifying material is introduced on the metal nanoparticle surface through the epoxide group.

* * * * *